(12) United States Patent
Couderc et al.

(10) Patent No.: US 8,520,203 B2
(45) Date of Patent: Aug. 27, 2013

(54) METHOD AND DEVICE FOR CHARACTERIZING MICROSCOPIC ELEMENTS

(75) Inventors: Vincent Couderc, Verneuil (FR); Philippe LeProux, Saint Pardoux (FR); Laurent LeFort, Limoges (FR); David Bouyge, Saint-Mexant (FR); Christelle Lesvigne-Buy, Les loges en Josas (FR); Aurelian Crunteanu Stanescu, Couzeix (FR)

(73) Assignees: C.N.R.S. Centre National de la Recherche Scientifique, Paris (FR); University de Limoges, Limoges (FR)

( * ) Notice: Subject to any disclaimer, the term of this patent is extended or adjusted under 35 U.S.C. 154(b) by 293 days.

(21) Appl. No.: 12/682,268

(22) PCT Filed: Oct. 10, 2008

(86) PCT No.: PCT/FR2008/001424
§ 371 (c)(1),
(2), (4) Date: Apr. 1, 2011

(87) PCT Pub. No.: WO2009/087287
PCT Pub. Date: Jul. 16, 2009

(65) Prior Publication Data
US 2011/0199609 A1 Aug. 18, 2011
US 2012/0038916 A2 Feb. 16, 2012

(30) Foreign Application Priority Data

Oct. 10, 2007 (FR) .................................... 07 07098

(51) Int. Cl.
*G01J 3/30* (2006.01)
(52) U.S. Cl.
USPC ........................................ 356/317; 356/300

(58) Field of Classification Search
USPC .................................................. 356/301–334
See application file for complete search history.

(56) References Cited

U.S. PATENT DOCUMENTS 5,294,799 A 3/1994 Aslund et al.
7,277,169 B2 * 10/2007 Ye et al. ........................ 356/317
(Continued)

FOREIGN PATENT DOCUMENTS
EP 1318389 A 6/2003

OTHER PUBLICATIONS

Siegel J et al: "Wide-field time-resolved fluorescence anisotropy imaging (TR-FAIM): Imaging the rotational mobility of a fluorophore" Review of Scientific Instruments, AIP, Melville, NY, US, vol. 74, No. 1, Jan. 1, 2003, pp. 182-192.

*Primary Examiner* — Gregory J Toatley
*Assistant Examiner* — Dominic J Bologna
(74) *Attorney, Agent, or Firm* — Brian L. Michaelis; Joseph M. Walker; Seyfarth Shaw LLP

(57) ABSTRACT

A method and device is provided for characterizing microscopic elements. A source signal may be chopped by means of microsystems of opto-electromechanical elements (MOEMS), which gives rise to temporal modulation of the excitation signals. The method of characterizing microscopic elements involves propagating a dispersed light source signal, spatially chopping the spectrum of the source signal into at least two excitation signals having predetermined wavelengths $\lambda_i$, coding the excitation signals, focusing the excitation signals in order to generate a sensor signal propagated towards a measurement zone, and analyzing an interaction signal issuing from the interaction of the sensor signal with the microscopic elements situated in the measuring space. The spatial chopping of the spectrum of the source light signal is performed by a microsystem of opto-electromechanical elements (MOEMS).

19 Claims, 2 Drawing Sheets

(56) References Cited

U.S. PATENT DOCUMENTS

| | | |
|---|---|---|
| 2003/0035197 A1* | 2/2003 | Ikeda et al. .................. 359/295 |
| 2003/0117618 A1* | 6/2003 | Itoh et al. ..................... 356/317 |
| 2004/0264847 A1* | 12/2004 | Koh et al. ....................... 385/22 |
| 2005/0046848 A1* | 3/2005 | Cromwell et al. ............ 356/417 |
| 2006/0139728 A1* | 6/2006 | Dyson et al. .................. 359/290 |
| 2007/0188750 A1* | 8/2007 | Lundquist et al. ............ 356/317 |
| 2008/0285041 A1* | 11/2008 | Ocelic et al. .................. 356/450 |

* cited by examiner

METHOD AND DEVICE FOR CHARACTERIZING MICROSCOPIC ELEMENTS

RELATED CASE INFORMATION

The present application claims benefit of PCT Application No. PCT/FR08/01424, filed Oct. 10, 2008 which claims benefit of French Application No. 0707098 filed Oct. 10, 2007.

FIELD OF THE INVENTION

The invention concerns a method and device for the qualitative and quantitative characterization of microscopic elements by multi-parameterized modulation of a source signal.

In this regard, the invention concerns the field of the analysis of microscopic elements, that is to say the characterization and counting of particles, molecules or cells passing at high speed in a light beam.

BACKGROUND OF THE INVENTION

In the prior art various solutions are known for analyzing the quantity of particles present in a fluid. In particular, flow cytometry consists of analyzing the optical or physical signals emitted by a particle intersecting the light beam of a laser or of an arc lamp in order to deduce there from the information on characterization and counting of the particles contained in the fluid.

Fluorescence analysis is generally carried out by means of the introduction and fixing of a large number of fluorescent markers, also referred to as fluorochromes, on different compounds of the solution. A specific excitation wavelength and therefore, potentially, an associated monochromatic light source corresponds to each fluorochrome.

Nevertheless, increasing the number of these markers is limited by the spectral overlap of the emission thereof. This is because overlap occurs when the fluorescence emission spectrum of a compound covers part of the emission spectrum of another compound.

To avoid this, several techniques can be used. The one used most often is the compensation method, which consists of reducing the fluorescence signal, or exciting signal, by the proportion of spectral overlap between two fluorochromes. Nevertheless, increasing the number of fluorochromes introduces significant complexity with regard to the analysis and consequently gives rise to a significant error rate on diagnosis.

One solution for overcoming these problems consists of introducing, on each excitation signal dedicated to a fluorochrome, a frequency modulation making it possible to identify the fluorescence emission by a frequency analysis in addition to chromatic analysis. For this purpose, an acousto-optical or electro-optical modulator can be used. This principle of multi-parameterized cytometric analysis has been the subject of several patent applications.

In particular U.S. Pre-Grant Publication No. 2003/0205682 is known, which describes the modulation of each wavelength at a given frequency. In addition, International Patent Application Publication No. WO 2006/111641 and U.S. Pre-Grant Publication No. 2004/0251436 disclose the use of acousto-optical modulators making it possible to select the wavelengths in a polychromatic light and to modify each of them specifically at a given frequency.

Frequency modulation, by means of acousto-optical or electro-optical modulators, gives rise to difficulty with regard to both the modulators and the light sources to be used. This is because the modulators have different characteristics according to the wavelength of use and must therefore be corrected for chromatic aberrations. In addition, the light source must have a sufficiently high emission frequency to obtain several analysis signals when the source signal is chopped. If the emission frequency is too low, the chopping of the source signal is limited and does not therefore make it possible to characterize sufficient markers.

Moreover, spectro-frequency modulation does not always make it possible to obtain reliable and satisfactory results, in particular when the number of fluorochromes is too high.

Finally, the use of acousto-optical modulators and laser sources having high emission frequencies represents high costs.

SUMMARY OF THE INVENTION

The aim of the present invention is to afford solutions to the aforementioned technical problems by presenting a device and method for characterizing microscopic elements that is reliable and inexpensive and makes it possible to obtain good results when the number of elements to be characterized is high.

In this regard, the invention makes provision for chopping the source signal by means of microsystems of opto-electromechanical elements, also called MOEMS, which gives rise to new possibilities of modulation, in particular temporal, of the excitation signals.

More precisely, the subject matter of the invention is a method of characterizing microscopic elements consisting in particular propagating a dispersed light source signal, spatially chopping the spectrum of the source signal into at least two excitation signals having predetermined wavelengths $\lambda_i$, coding the excitation signals, focusing the excitation signals in order to generate a sensor signal propagated to a measuring space, and analyzing an interaction signal issuing from the interaction of the sensor signal with the microscopic element situated in the measuring space. The spatial chopping of the spectrum of the source light signals is carried out by a system of elements with opto-electromechanical micromirrors (MOEMS).

Preferably, the step of chopping the excitation signals is preceded by a phase of selecting the spectral width of these excitation signals.

Advantageously, the step of coding the excitation signals comprises a phase of temporal modulation of the excitation signals, in particular by retarding at least one excitation signal and/or by phase modulation of at least one excitation signal, a phase of frequency modulation of the excitation signals, in particular by switching of the MOEMS and/or a phase of modulation of the polarization of the excitation signals.

The invention also relates to a device for characterizing microscopic elements for implementing the method defined above, the device comprising a means of emitting a dispersed light source signal, a spectrum chopper able to divide the spectrum of the source signal into at least two excitation signals of predetermined wavelengths $\lambda_i$, means of coding the excitation signals, a measuring space in which a sensor signal including the excitation signals is propagated and means of analyzing an interaction signal issuing from the interaction of the sensor signal with the microscopic elements situated in the measuring space. The spectrum chopper is a microsystem of elements with opto-electromechanical micromirrors (MOEMS).

Advantageously, the opto-electromechanical elements comprise means of selecting the spectral width of the excitation signals.

Preferably, the opto-electromechanical elements are of the bridge or cantilever type, substantially triangular in shape and/or deformable achromatic mirrors.

Advantageously, the device has color filters in front of the opto-electromechanical elements. Preferably, the device has means of coding the excitation signals by temporal modulation.

According to an advantageous embodiment, the temporal modulation coding means are delay lines. Preferably, the device has means of phase modulation of the excitation signals.

Advantageously, the phase modulation means consist of a piezoelectric modulator for periodically stretching the delay lines.

Advantageously, the device has means of coding the excitation signals by frequency modulation.

According to one embodiment, the microsystem comprises electromechanical actuators for switching the opto-electromechanical elements in order to effect the frequency modulation of the excitation signals.

Preferably, the device has means of coding the excitation signals by modulation of the polarization.

According to an example embodiment, the light source is a pulse-type white source.

MOEMS technology, already implanted in other fields of application, is a mature technology having the advantages of being precise, inexpensive and compact.

MOEMSs make it possible to precisely chop the source signal into a multitude of excitation signals having predetermined wavelengths $\lambda_1$.

They also make it possible to spatially address these excitation signals, synchronously or not, on several analysis windows, which makes it possible to envisage analyses in parallel.

Finally, MOEMSs can be used to generate temporal and/or frequency modulation, by pulse switching.

The use of MOEMSs of the triangular-profile cantilever type makes it possible to modify the spectral width of the excitation signals without modifying the center wavelength $\lambda_i$ thereof. The result is a modification and adjustment of the power spectral density (light flux per unit of spectrum) of the excitation signals.

Microsystems of opto-electromechanical elements of the cantilever type are advantageous since the control voltages to be applied are low.

Microsystems of electronic elements of the bridge type have a high activation speed and a frequency ranging up to 200 kHz, which makes it possible to increase the sampling frequency of the device.

The use of filters in front of the opto-electronic elements introduces an additional degree of freedom with regard to the light flux desired.

Temporally modulating the excitation signals, in addition to spectral modulation and any other pre-existing modulations, makes it possible to obtain a more reliable diagnosis by cross checking of the results and to analyze a larger number of microscopic elements. This is because this temporal modulation dispenses with the problems related to the spectral overlap of the fluorochromes.

Supplementary modulations, in particular of the frequency and polarization type, make it possible to characterize a larger number of microscopic elements and make the analysis more reliable by cross checking of the results.

Moreover, the use of optical fibers of mechanically adjustable length makes it possible to add time coding and phase modulation to the excitation signals.

The use of a pulse-type white source with a temporal modulation of the excitation signals limits the cost of the device according to the invention without reducing the performance thereof.

BRIEF DESCRIPTION OF THE DRAWINGS

Other features and advantages of the invention will emerge from the following reading of a detailed example embodiment, with reference to the figures, which show respectively.

DETAILED DESCRIPTION OF THE INVENTION

Figure 1:
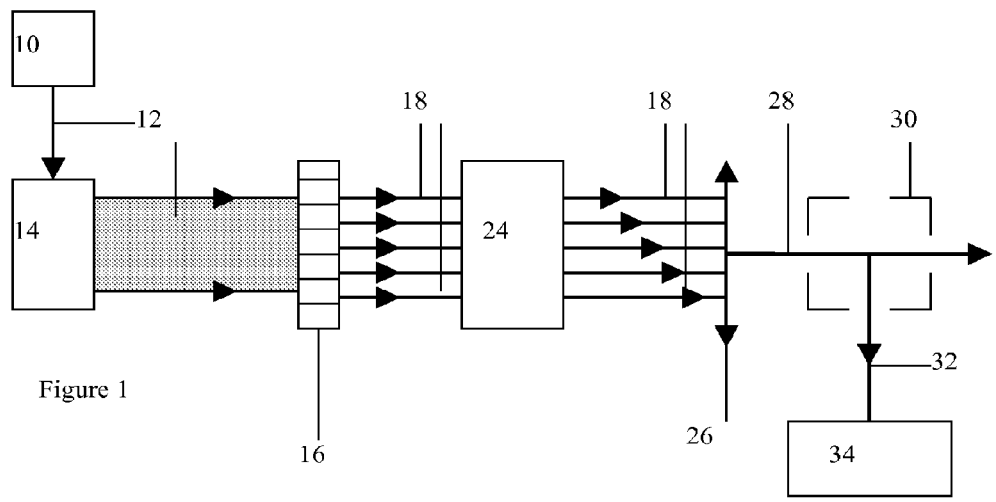
FIG. 1, a schematic view of a first example embodiment of a device for characterizing microscopic elements according to the invention.

An example embodiment of a method of characterizing microscopic elements according to the invention will now be described, with reference to FIG. 1.

In this example embodiment, the microscopic elements are characterized by flow cytometry, referred to as fluorescence cytometry. The microscopic elements are therefore marked by fluorochromes capable of emitting fluorescence light after excitation.

The first step of the method consists of propagating and spatially dispersing, by emission 10 and dispersion 14 means, a light-source signal 12, coherent or partially coherent.

The spectrum of the dispersed signal 12 is then chopped spatially by chopping means 16 into several excitation signals 18 having wavelengths $\lambda_i$ corresponding to the excitation wavelengths of the fluorochromes fixed on the microscopic elements to be analyzed.

According to the invention, the means 16 of chopping the source signal 12 consist of a microsystem of opto-electromechanical elements (described in detail below, but not shown in FIG. 1).

The excitation signals 18 are then coded by coding means 24. Thus each excitation signal is modulated in time, frequency and/or polarization.

Preferably, the modulation of the excitation signals 18 is performed by switching of the opto-electromechanical elements.

The coded excitation signals 18 are then focused by focusing means 26 in order to generate a sensor signal 28 having low dispersion. The sensor signal 28 is then propagated to a measuring zone 30 containing the microscopic elements to be analyzed.

The interaction of the sensor signal 28 with the microscopic elements containing the fluorochromes generates an interaction signal 32 making it possible to characterize the elements contained in the measuring space 30.

The interaction 32 is then directed to analysis means 34 that define the characteristics of the microscopic elements analyzed.

A second example embodiment of the invention will now be described with reference to FIGS. 2 and 3.

In this second example embodiment, the emission means 100 is a light source 102 coupled to a first half-wave plate 104 and a polarizer 106.

The light source 102 emits a source signal 120 in the form of a pulse-type laser signal producing a radiation of 1064 nanometers and pulses lasting 600 picoseconds, with a repetition frequency of around 6 kHz.

The mean power of the light source 102 is 45 milliwatts, which corresponds to a peak power per pulse of around 12.5 kilowatts.

The association of the plate and polarizer 106 makes it possible to increase or decrease the power of the source signal 120 by modifying the orientation of the half-wave plate 104.

The polarization of the source signal 120 is then oriented linearly by means of a second half-wave plate 108 and then focused by a lens 110 with a focal length of two millimeters towards a linear waveguide, for example of the air/silica microstructured fiber type.

This architecture makes it possible to extend the spectrum of the source signal 120 in the visible region.

Advantageously, the source signal 120 has flatness of around 3 decibels over a spectral band extending for example from 400 to 750 nanometers.

According to a variant embodiment, the emission means 100 comprises a subnanosecond light source of the microlaser type that emits a source signal 120 in the form of a pulse-type wide-band white light that is coherent or partially coherent. This solution has the advantage of increasing the power density of the source while minimizing the costs of the device.

The source signal 120 is then dispersed spatially by a dispersion means 140. Thus the source signal 120 is collimated by means of a microscope lens 142 and then dispersed by a prism 144 having high transmission in the region of the visible wavelengths and ultraviolet, and finally collimated by means of a cylindrical lens 146 having a focal length of approximately 50 millimeters.

The dispersed source signal 120 is then directed to the chopping means 160 able to divide the sensor signal 120 into several excitation signals 180 having wavelengths $\lambda_i$ corresponding to the excitation wavelengths of the fluorochromes fixed on the microscopic elements to be analyzed.

According to the invention, the chopping means 160 comprise at least one microsystem 200 of opto-electromechanical elements 220.

The microsystem 200 has twelve deformable opto-electromechanical elements 220 each comprising an electromechanical actuator. The opto-electromechanical elements 220 advantageously have a wide-band reflective covering 222 such as an achromatic mirror.

According to a variant, it is possible that the reflective covering 222 is produced by deposition of a dichroic mirror so as to restrict the bandwidth of the signals 180 reflected.

The reflective covering 222 is alternatively a membrane made from gold, silver or aluminum, which makes it possible to benefit from a wide-band reflectivity ranging from ultraviolet to infrared. Moreover, these elements are achromatic, which is essential in such an optical device.

The microsystem 200 of opto-electromechanical elements 220 divides the dispersed source signal 120. The reflective covering 222 of the opto-electromechanical elements 220 reflects excitation signals 180 corresponding to the excitation wavelengths $\lambda_i$ of the fluorochromes fixed to the microscopic elements to be analyzed.

The number of excitation signals 180 chopped is equal to the number of opto-electromechanical elements 220 used.

In this example embodiment, the microsystem 200 of opto-electromechanical elements 220 has a battery of twice six opto-electromechanical elements 220. The spectral width of the excitation signals 180 is fixed by spectral stretching carried out by the prism 144 and by the width of the reflective coverings 222 of the microsystem 200 of opto-electromechanical elements 220.

In addition, the device may also comprise color filters 224 disposed in the spectral plane in front of the reflective coverings 222 of the opto-electromechanical elements 220. The filters 224 thus introduce an additional degree of freedom with regard to the required light flux.

These opto-electromechanical elements 220 can be actuated synchronously or asynchronously. This actuation is controlled by a multitrack electronic control module 228.

According to one embodiment, the microsystem 200 of opto-electromechanical elements 220 is of the cantilever type. Thus the control voltages to be applied are around 4 to 20 volts, and the recurrence frequency may range up to approximately 10 kilohertz.

According to an alternative embodiment, the opto-electromechanical elements 220 are of the bridge type, that is to say they are anchored at their two ends. This geometry increases the activation speed of the electromechanical actuators until frequencies of 200 kilohertz are reached.

Figure 3:
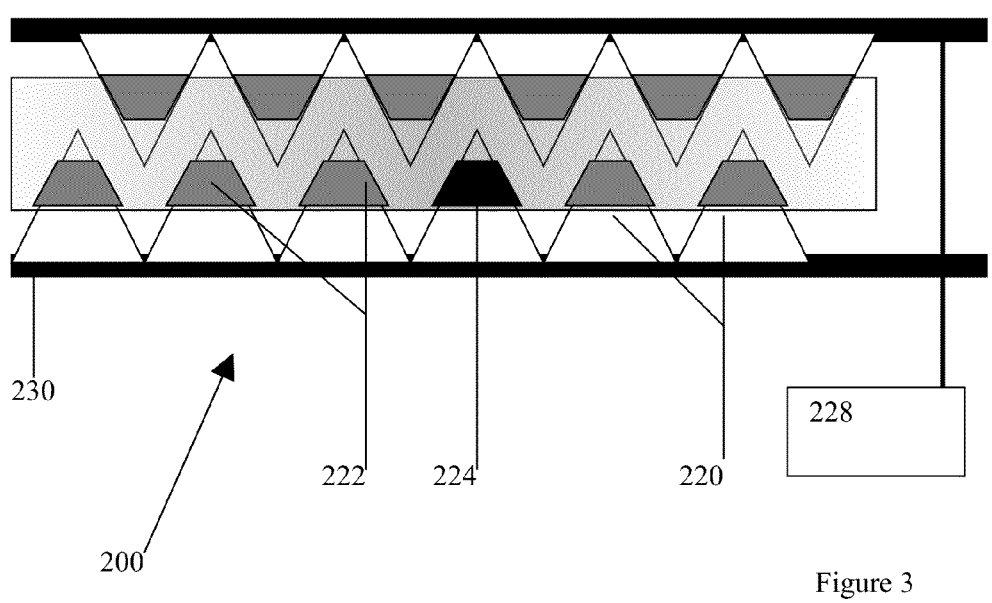
FIG. 3, a schematic view of an embodiment of microsystems of opto-electromechanical elements belonging to a device for characterizing microscopic elements according to the invention.

Finally, according to a third embodiment shown in FIG. 3, the opto-electromechanical elements 220 are of the cantilever type and have a substantially triangular shape. These opto-electromechanical elements 220 are disposed along the two bars 230 placed side by side. Thus the opto-electromechanical elements 220 of the first bar 230 are embedded in the opto-electromechanical elements 220 of the second.

The longitudinal position of the bars 230 is adjustable with respect to the location of the spectrum of the source signal 120 so as to enable the center wavelength $\lambda_i$ of each excitation signal 180 to be modified, by longitudinal movement of the bars 230.

Moreover, the transverse separation of the two bars 230 is also adjustable so that it is possible to modify the spectral width of each excitation signal 180, without the centre wavelength $\lambda_i$ being modified.

According to a variant, the shape of the optoelectronic elements is trapezoidal, which makes it possible to obtain the same results as before.

Each excitation signal 180 is advantageously frequency modulated. This modulation is managed by the electronic control module 232 of the microsystem 200, which allocates a specific switching frequency w, to each switch of the opto-electromechanical element 220 concerned. Thus the excitation signal 180 associated with this opto-electromechanical element 220 is coded by frequency modulation.

According to an example embodiment, the pulse laser 102 has a pulse frequency $F_L$ equals to one megahertz. The frequency modulation results in the sampling of a pulse in a regular manner in time. The sampling frequency, equal to the switching frequency $F_i$, is then less than the pulse frequency ($F_1=F_L/2$, $F_2=F_L/3$, $F_3=F_L/5$, etc).

Thus, from a frequency of one megahertz, the sampling of one pulse out of two or of one pulse out of three leads to a modulation of 500 kilohertz and 333 kilohertz respectively.

The excitation signals 180 are then sent to temporal coding means 242. The temporal coding means 242 are here optical fibers, or delay lines, having a predetermined length $\Delta_i$ in order to delay each excitation signal 180 temporally.

The device also comprises means 244 of modulating the phase of the excitation signals 180 so as to periodically change the length of each fiber by mechanical stretching. According to one example embodiment, these phase modulation means consist of piezoelectric modulators which, by means of periodic electrical pulses, make it possible to mechanically stretch the length of the delay fibers. Each fiber being stretched at a specific frequency, the excitation signals have a phase modulation.

Alternatively, the phase modulation means can consist of any other means of stretching the delay fibers, in particular by means of magnetosensitive elements.

Time coding means here causing, for each excitation signal 180, a unique delay. The unique delay makes it possible to grant to each fluorochrome a particular time window enabling it to partially or totally de-excite. Thus the fluorochromes are acted on successively so as to prevent a temporal overlap of the interaction signals 320.

For example, a fluorochrome having a fluorescence time of two nanoseconds is excited by an excitation signal 180 of 600 picoseconds, at a wavelength of 488 nanometers. In order to be able to identify the fluorescence signal, or interaction signal 320, issuing from this particular fluorochrome, the following excitation signal 180 is retarded by more than 2 nanoseconds by passage through a fiber having a longer wavelength than the others. Here the delay of 2 nanoseconds is obtained with a fiber with a length of 0.6 meters.

The delay introduced between each excitation signal 180 is then a function of the fluorescence time of each fluorochrome.

In addition, phase modulation coding means, for each excitation signal 180, causing a small periodic variation in the temporal delay. This temporal delay modulation is equivalent to a phase modulation of the signal and can be detected by the analysis system 340. Thus this modulation makes it possible to differentiate the fluorescence issuing from two fluorochromes that have been excited synchronously.

The excitation signals can also be coded by modulation of their polarization. Analysis of their polarization then makes it possible to obtain information complementary to that obtained by a wavelength analysis or according to the decay time of the fluorescence.

Means of modulation by polarization are for example described in the following documents:

Klaus Suhling, Paul M. W. French and David Philips: Time-resolved fluorescence microscopy, Photochem. Sci., 2005, 4, 13-22, DOI: 10.1039/b412924p.

Gaponenko, S. V.; Germanenko, I. N.; Stupak, A. P.; Eyal, M.; Brusilovsky, D.; Reisfeld, R; Graham, S; Klingshirn: C. Fluorescence of Acridine Orange in inorganic glass matrices. Applied Physics B, vol. 58, issue 4, p. 283-288 (1994).

The second example embodiment of the device according to the invention also comprises means of coding by polarization modulation 250 of the excitation signals 180.

These means of coding by polarization modulation 250 make it possible to control the orientation of the polarization vector of the wave of the excitation signal 180 that excites the fluorochromes included in the microscopic elements analyzed.

Means of coding by polarization modulation 250 must therefore be understood to be means that make it possible to orient the polarization of the excitation signal 180 vis-à-vis the sample to be analyzed.

Figure 2:
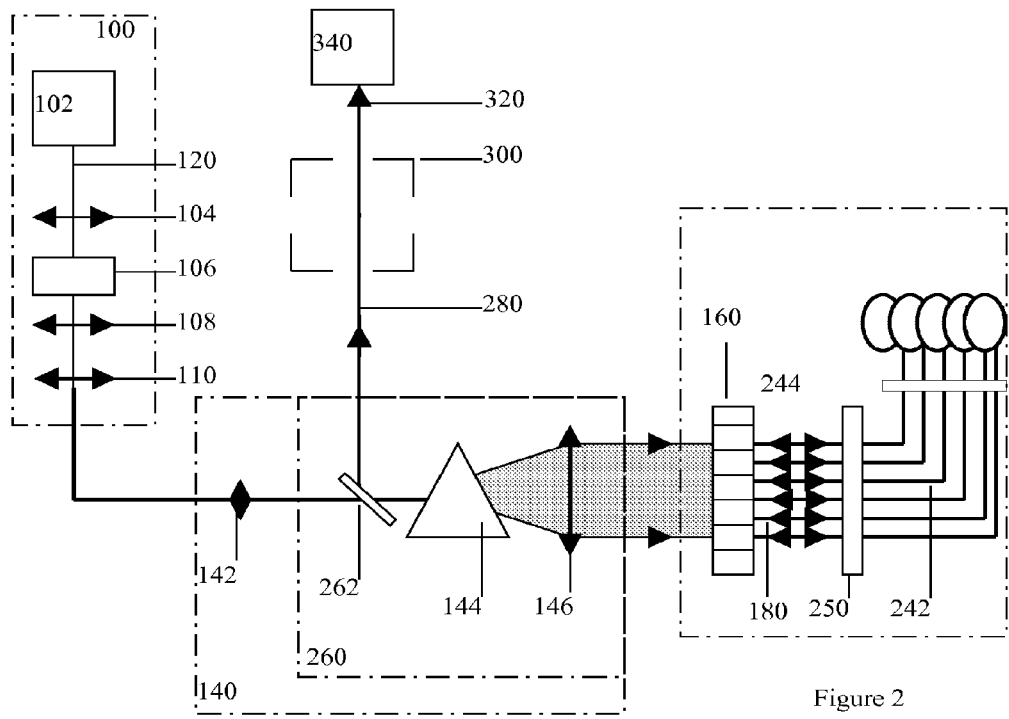
FIG. 2, a schematic view of a second example embodiment of a device for characterizing microscopic elements according to the invention.

In the example embodiment presented in FIG. 2, the light source 102 is polarized linearly. The orientation of the polarization is obtained by means of the second half-wave plate 108. Moreover, the optical fibers used are of the polarization maintenance type. The delay lines therefore exhibit birefringence.

Thus the orientation of the excitation signals 180 is controlled at the output of the delay lines 242 by controlling the orientation of the end of said delay lines 242. Each excitation signal 180 then has a particular orientation of its polarization vector.

According to a variant embodiment, the means of coding by polarization modulation 250 are composed of half-wave plates.

Once coded, the excitation signals 180 are re-sent in the opposite direction, towards the lens 146 and prism 144 which, coupled to a mirror 262 oriented at 45 degrees, serve as focusing means 260.

At the exit from these focusing means, the sensor signal 280 carries information coming from the coded excitation signals 180. The sensor signal 280 is then directed towards the measuring space 300 and, by interaction with the microscopic elements to be analyzed containing the fluorochromes, generate an interaction signal 320.

The interaction signal 320 is analyzed by analysis means 340 that take account of the parameters mentioned above in order to characterize the microscopic elements included in the sample to be analyzed.

Advantageously, the analysis means comprise firstly dichroic mirrors and polarizers (not shown), which firstly enables the various wavelengths contained in the interaction signal 320 to be separated.

A photomultiplier or a sensitive diode then converts each interaction signal 320 into an electrical signal which, by means of a multivoice oscilloscope and/or an electrical spectrum analyzer, provides information on the decay time of the fluorescence issuing from the fluorochromes and on the amplitude and the oscillation frequency of the various interaction signals 320.

Many fluorescence analysis techniques applicable in the context of the invention are for example described in the following publications:

Biological Imaging and Sensing; T Furukawa, ISBN: 9783540438984;

Fluorescence intensity and lifetime distribution analysis: Toward higher accuracy in fluorescence fluctuation spectroscopy; Biophysical Journal, August 2002 by Paulo, Kaupo, Brand, Leif, Eggeling, Christian, Jager, Stefan, et al;

Flow Cytometry Data analysis Basic Concepts and Statistics; By James V. Watson, published in 1992 ISBN 0521415454.

The invention is not limited to the example embodiments described and shown above. A person skilled in the art is in a position to effect various combinations of the method and device mentioned above without departing from the scope of the invention.

Thus the characterization of the elements can be carried out equally well by fluorescence or phosphorescence or by diffusion, diffraction or absorption. Combined analysis of these various parameters is also possible.

Moreover, the temporal coding, phase modulation and polarization means could also be incorporated in the microsystem 200 of opto-electromechanical elements 220.

What is claimed is:

1. A method of characterizing microscopic elements comprising:
propagating a dispersed light source signal,
spatially chopping the spectrum of the source signal into at least two excitation signals having predetermined wavelengths $\lambda_i$,
coding the excitation signals,
focusing the excitation signals in order to generate a sensor signal propagated towards a measuring space;

analyzing an interaction signal issuing from the interaction of the sensor signal with the microscopic elements situated in the measuring space; and wherein the spatial chopping of the spectrum of the source signal is carried out by a microsystem of elements with opto-electromechanical elements and the step of chopping the excitation signals is preceded by a phase of selecting the spectral width of these excitation signals, wherein the opto-electromechanical elements are of a cantilever type, are substantially triangular in shape and are disposed along first and second longitudinally and transversely adjustable bars placed side by side such that the opto-electromechanical elements of the first bar are embedded in the opto-electromechanical elements of the second bar.

2. The method according to claim 1, wherein the coding step comprises a phase of temporal modulation of the excitation signals.

3. The method according to claim 2, wherein the temporal modulation of the excitation signals consists of delaying at least one excitation signal by a predetermined value.

4. The method according to claim 3, wherein the temporal modulation comprises a phase of phase modulation of at least one excitation signal.

5. The method according to claim 1, wherein the coding step comprises a phase of frequency modulation of the excitation signals.

6. The method according to claim 5, wherein the frequency modulation is carried out by switching of the opto-electromechanical elements of the microsystem.

7. The method according to claim 1, wherein the coding step has a phase of modulation of the polarization of the excitation signals.

8. A device for characterizing microscopic elements comprising:
a means of emitting a dispersed light-source signal;
a spectrum chopper able to divide the spectrum of the source signal into at least two excitation signals with predetermined wavelengths $\lambda_i$;
means of coding the excitation signals;
a measuring space in which a sensor signal is propagated, grouping together the excitation signals;
means of analyzing an interaction signal issuing from the interaction of the sensor signal with the microscopic elements situated in the measuring space; and
wherein the spectrum chopper is a microsystem of elements with opto-electromechanical elements comprising means of selecting the spectral width of the excitation signals,
wherein the opto-electromechanical elements are of a cantilever type, are substantially triangular in shape and are disposed along first and second longitudinally and transversely adjustable bars placed side by side such that the opto-electromechanical elements of the first bar are embedded in the opto-electromechanical elements of the second bar.

9. The device according to claim 8, wherein the opto-electromechanical elements are deformable achromatic mirrors.

10. The device according to claim 8, comprising: at least one color filter in front of the opto-electromechanical elements.

11. The device according to claim 8, comprising: means of coding by temporal modulation of the excitation signals.

12. The device according to claim 11, wherein the means of coding by temporal modulation are delay lines.

13. The device according to claim 12, comprising: means of phase modulation of at least one excitation signal.

14. The device according to claim 13, wherein the phase modulation means consist of at least one piezoelectric modulator for periodically stretching at least one of the delay lines.

15. The device according to claim 8, comprising: means of coding by frequency modulation of the excitation signals.

16. The device according to claim 15, wherein the microsystem comprises electromechanical actuators for switching the opto-electromechanical elements in order to effect the frequency modulation of the excitation signals.

17. The device according to claim 8, comprising: means of coding by modulation of the polarization of the excitation signals.

18. The device according to claim 8, wherein the light source is a pulsed white light source.

19. A device for characterizing microscopic elements comprising:
a means of emitting a dispersed light-source signal;
a spectrum chopper able to divide the spectrum of the source signal into at least two excitation signals with predetermined wavelengths $\lambda_i$;
means of coding the excitation signals;
a measuring space in which a sensor signal is propagated, grouping together the excitation signals;
means of analyzing an interaction signal issuing from the interaction of the sensor signal with the microscopic elements situated in the measuring space; and
wherein the spectrum chopper is a microsystem of elements with opto-electromechanical elements comprising means of selecting the spectral width of the excitation signals,
wherein the opto-electromechanical elements are of a bridge type and are disposed along first and second longitudinally and transversely adjustable bars placed side by side such that the opto-electromechanical elements of the first bar are embedded in the opto-electromechanical elements of the second bar.

* * * * *

UNITED STATES PATENT AND TRADEMARK OFFICE
CERTIFICATE OF CORRECTION

PATENT NO. : 8,520,203 B2
APPLICATION NO. : 12/682268
DATED : August 27, 2013
INVENTOR(S) : Couderc et al.

Page 1 of 1

It is certified that error appears in the above-identified patent and that said Letters Patent is hereby corrected as shown below:

On the Title Page Item (73) Assignee name is misspelled. Please correct the name
    'University de Limoges' to 'Universite de Limoges'

Signed and Sealed this
Twelfth Day of November, 2013

Teresa Stanek Rea
*Deputy Director of the United States Patent and Trademark Office*